United States Patent
Shubin

Patent Number: 5,807,360
Date of Patent: *Sep. 15, 1998

[54] DEVICE FOR DISCREET SPERM COLLECTION

[76] Inventor: Steven A. Shubin, 801 N. Weston La., Austin, Tex. 78733

[*] Notice: The term of this patent shall not extend beyond the expiration date of Pat. No. 5,782,818.

[21] Appl. No.: 722,475

[22] Filed: Sep. 27, 1996

[51] Int. Cl.$^6$ ................................................ F25D 23/12
[52] U.S. Cl. ........................ 604/349; 600/38; 128/897
[58] Field of Search .................... 128/760, 897, 128/917; 600/38; 604/349; 62/457.1–457.4; 220/625, 739

[56] References Cited

U.S. PATENT DOCUMENTS

| | | | |
|---|---|---|---|
| 2,757,517 | 8/1956 | Goldberg | 62/457.4 |
| 4,393,975 | 7/1983 | Moore | 62/457.2 |
| 4,741,176 | 5/1988 | Johnson et al. | 62/457.4 |
| 5,005,374 | 4/1991 | Spitler | 62/457.2 |
| 5,458,559 | 10/1995 | Gauntlett | 600/38 |

*Primary Examiner*—Robert A. Clarke
*Attorney, Agent, or Firm*—John S. Munday; Stephen G. Stanton

[57] ABSTRACT

A device useful for collection of sperm from human males, preferably in a discreet and camouflaged manner. The device includes an outer shell having a generally tubular inside chamber and an exterior with the appearance of an ordinary device normally found in a public environment such as one having the appearance of a flashlight. The shell provides access to the chamber via at least one removable cap having an exterior appearance compatible with the ordinary device. The chamber is filled by an insert formed from an elastomeric gel having the general tactile feel of human flesh. One end of the insert has an opening simulating a body orifice. The insert includes a central passage sized to accommodate a human male sex organ in said opening while providing at least a cushioning amount of the elastomeric gel. A preferred insert includes radially extending high points for engagement with the chamber and radially extending low points for expansion of the central passage during use. The preferred elastomeric gel is formed from a mixture of plasticizing oil and a block copolymer selected from styrene ethylene butylene styrene block copolymers and styrene ethylene propylene styrene block copolymers. The preferred elastomeric gel is formed from a mixture of 5–9% by weight of the block copolymer and 90–94% by weight of the plasticizing oil, and trace amounts of pigments and fillers.

12 Claims, 6 Drawing Sheets

DEVICE FOR DISCREET SPERM COLLECTION

FIELD OF THE INVENTION

The present invention relates to a device for discreet and camouflaged collection of sperm from human males. More particularly the present invention relates to a device having an outward appearance that is innocuous and portable that may be used by adult males for the collection of sperm at appropriate locations and which can also be stored in the home without provoking the curiosity of children.

BACKGROUND OF THE INVENTION

In my prior patent, U.S. Pat. No. 5,466,235, I disclose a construction of a female functional mannequin for use by adult males. The device is shown to be useful as a simulation of a female in a functionally operative mannequin for use by a male to deposit sperm, whether for medical or personal purposes. As noted in my patent, such mannequins could be used within sperm banks and also by psychiatrists in treating people with sexual disorders. Other uses are to decrease the transmission of AIDS and other sexually transmitted diseases and also, perhaps, to decrease prostitution and, possibly, even rape and molestation. It is also noted that such mannequins could be used by people incarcerated within jails, by persons with certain disabilities or, for whatever reason, do not have access to a human female partner.

The device of my prior patent includes a torso of the human female, in which a rigid frame duplicates the pelvic bone structure while other materials duplicate the muscle layer and skin of the human female. A cavity is located in the area of the crotch, into which is inserted a cartridge designed to simulate a human orifice. Mounted within the interior chamber of the cartridge is an elastomer that has been impregnated with mineral oil to decrease friction upon an exterior object being inserted through an opening formed in the elastomer.

While my patent succeeds admirably in fulfilling the objects of that invention, it has several characteristics that prevent it from universal acceptance. When the torso mannequin is used in sperm banks, doctor's offices, and other public facilities, it is sometimes intimidating to the patient being treated or may have an adverse affect upon the patient's sexual desire and ability to deposit sperm. Some persons find the device to be positive in its stimulative effect while others do not.

When the device of my patent is used in the home, or by those who find such a mannequin to be positive in nature, there is the concern that others will still find the object during a casual visit to the home. More importantly, when such a device is kept in a home with children, extreme caution must be exercised to prevent the natural curiosity of the child to lead him or her to find the female mannequin torso. Not only will legitimate uses by the father, for example, be embarrassing to the parents and the children, there is the risk that the child might be tempted to play with the mannequin, either innocently or not. In either case, it is an inappropriate device for children in virtually all cases and must be stored in nearly absolute security.

As noted in my prior patent referred to above, the material that is incorporated in the cartridge is generally described as an elastomer, roughly eight and a half inches long, three inches in width and five inches deep. The elastomer is characterized as being a gel that is a copolymer such as a polystyrene plastic mixed within mineral oil in a ratio of three to four hundred percent greater mineral oil, by weight, than the elastomer. However, at the time that my previously identified patent issued, namely in November, 1995, a fully satisfactory, stand alone gel that could be formed into the elastomer of my invention and utilized repeatedly while duplicating penetration characteristics of a human orifice was not available. My prior patent contemplated the use of a wide variety of elastomeric gels without regard to the stability of the gel during repeated use or the characteristics of its surface that might be in contact with the male sex organ.

Accordingly, it is an object of the present invention to provide a device that permits use by a male in relatively public circumstances such as sperm banks, doctors offices and the like, where privacy is not the only consideration for appropriate motivation.

Another object of this invention is to provide a device that is innocuous or innocent in appearance but which can serve to provide a discreet means for achieving the deposit of sperm in a way that it may be collected.

Yet another object of the present invention is to provide an elastomer capable of use as a simulated human orifice, such that the orifice duplicates penetration characteristics of that orifice.

Other objects will appear hereinafter.

SUMMARY OF THE INVENTION

It has now been discovered that the above and other objects of the present invention may be accomplished in the following manner. Specifically, the present invention provides a device that has an innocuous appearance, such as that of a flashlight, thermos or other cylindrical product normally found in the home or office. The inside of the device is filled with a stable gel that is unaffected by prolonged use, is easily cleaned and sanitized, and has characteristics such as resistance, texture and tactile feel that replicate human orifices.

In its simplest form, the present invention comprises an innocuous device, such as a flashlight, thermos or the like, having a generally cylindrical configuration and with removable caps or lids at one or both ends of the device. The interior of the device is provided with a chamber adapted to receive a container having a quantity of an elastomeric gel therein. The container and elastomeric gel are configured to provide access to the male sex member for penetration, such that the portion of the elastomeric gel in contact with that member has a surface texture that replicates a human body orifice, most typically the female sex organ, but all other orifices of a human body are within the scope of this invention. In addition to the vagina, the rectal region and the mouth or lips may be depicted. The visible opening of the gel may be configured to resemble one of the orifices or may have no appearance other than the opening that is to be used.

The user merely removes the cap or lid at both ends of the device into which the gel has been placed, and proceeds to use the device as intended. As can be understood, movement of an object within an object is affected by the presence of air within the object, particularly if the air is confined. Accordingly, removing both end caps allows for release of entrained air in the gel's central passage.

In one embodiment, a collection chamber may be provided at the other end of the device. In this manner, sperm may be collected, such as at a sperm bank or doctor's office, by removing the cap at the collection end to have access to the collection chamber. Alternatively, the inside or bottom end may be closed so that the insert will be removed and the contents emptied into a container. Since it is good practice to clean the insert after each use, this may be the preferred method of collection.

In another embodiment, the device may also include a small heating element and a battery so that the elastomeric gel may be heated to approximately normal body temperature, to further increase the realistic feel of the gel.

A preferred elastomeric gel for use with the present invention should have the following characteristics. The gel should be soft and flexible so as to simulate the inside of female sex organ. To do this, it is necessary to have a degree of lubrication in the gel to achieve the proper friction characteristics while maintaining the elastic memory of the gel and prevent permanent deformation. The gel should also have the tactile feel of human flesh. It should be stable and capable of multiple washings or cleanings without deterioration.

BRIEF DESCRIPTION OF THE DRAWINGS

For a more complete understanding of the invention, reference is hereby made to the drawings, in which.

DETAILED DESCRIPTION OF THE PREFERRED EMBODIMENT

Figure 1:
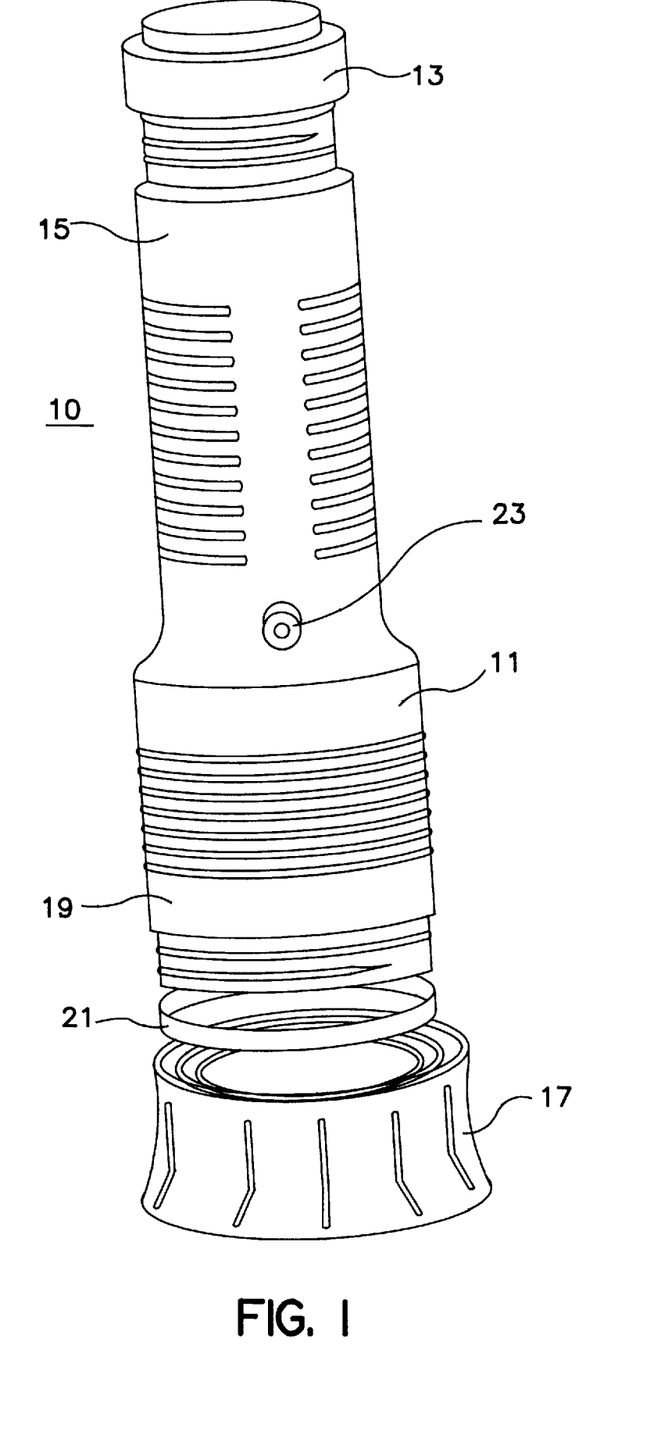
FIG. 1 is a perspective view of the preferred embodiment illustrating its outer appearance, all in accordance with the invention.

As shown in the drawings, a device useful for discreet and camouflaged collection of sperm from human males is shown generally at 10, and having an outer shell, in this case as a flashlight 11, having a generally tubular inside chamber and an exterior with the appearance of an ordinary device normally found in a public environment. Flashlight 11 includes a first end cap 13 that is threaded on to small end 15. A simulated lens cap end 17 also threads onto flashlight 11 at the large end 19, and may included an o-ring 21 or other fluid sealing means.

Other ordinary devices such as thermos bottles, bottles for containing liquids to be consumed, such as medicines or beverages, some shapes of portable radios, and endless other objects commonly found in homes, offices, and medical facilities. All that is needed is a shape that can accept a generally tubular inside chamber, although the outside may not have a tubular shape. It is, of course, necessary that the device be of a size to be used by the persons for whom it is intended.

Figure 2:
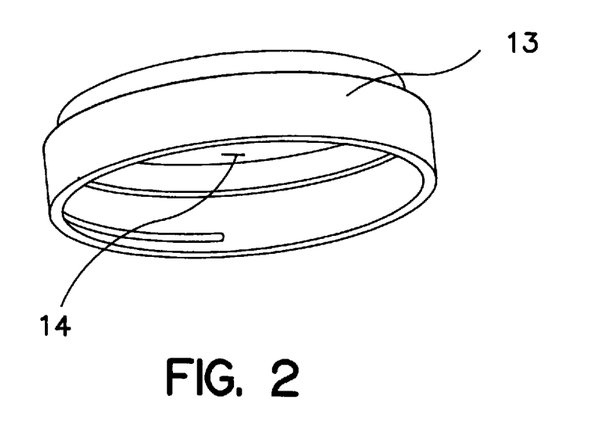
FIG. 2 is a perspective view of one end cap of the device shown in FIG. 1.
Figure 3:
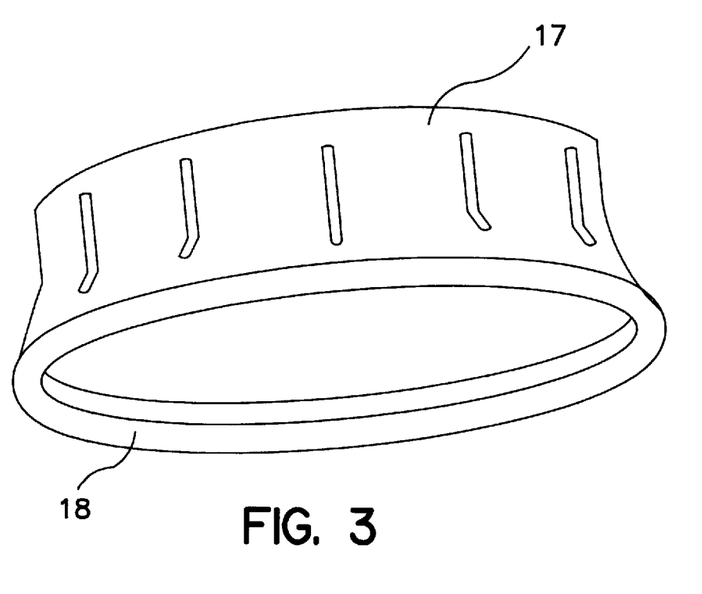
FIG. 3 is a perspective view of the other end cap of the device shown in FIG. 1.

Both small cap 13 in FIG. 2 and lens cap end 17 in FIG. 3 have closed surfaces 14 and 18 respectively, that realistically replicate the appearance of a real, functioning flashlight. Switch button 23 is also provided for realism, and may be non-functional to convey the idea that the flashlight is no longer operable, or it may function, without actually producing light from the flashlight, to convey the idea that the batteries need to be replaced. When the device is used, both end cap 13 and lens cap end 17 are removed as described below.

Figure 4:
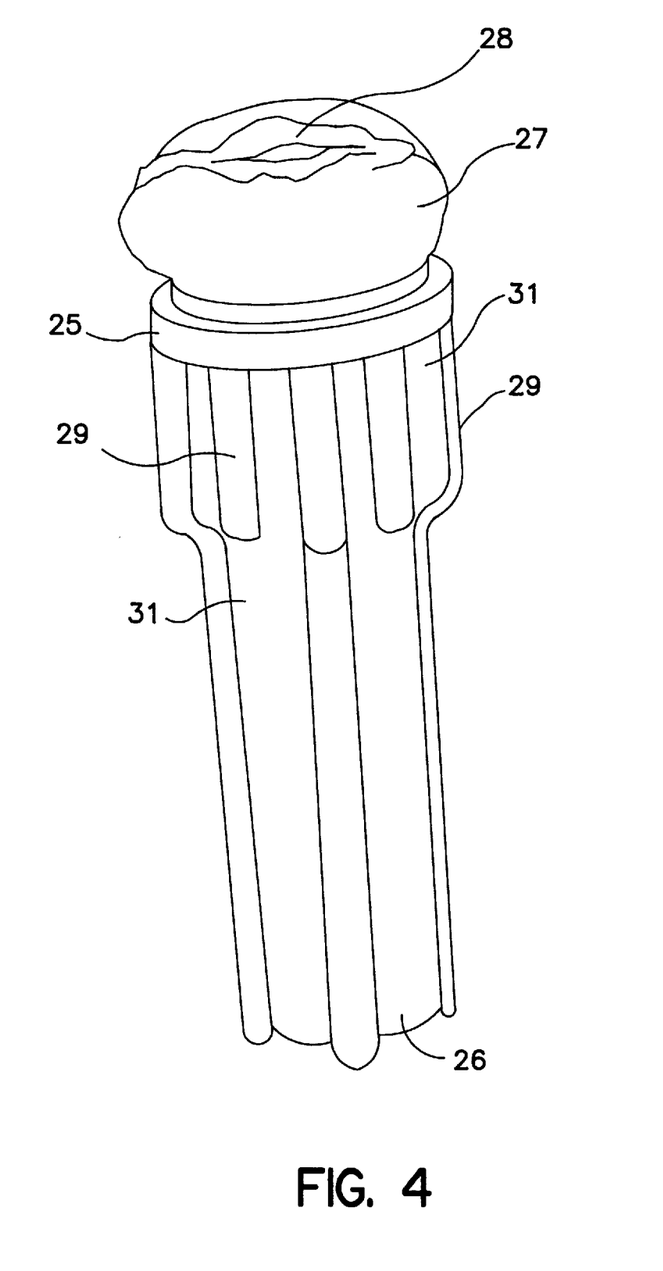
FIG. 4 is a perspective view of the preferred insert or interior portion of the device shown in FIG. 1, illustrating its outer appearance.

FIG. 4 illustrates an insert 25 for use in the interior of flashlight 11. Insert 25, formed from an elastomeric gel having the general tactile feel of human flesh, includes a first end 26 for insertion into the flashlight as described below and a second end 27 having the general appearance of a female body orifice. End 27 is positioned to be exposed upon removal of cap 17. Alternatively, end 27 may have no appearance other than the opening that is to be used.

The elastomeric gel that insert 25 is formed from has a human flesh-like texture or tactile feel. It is preferably formed from a mixture of plasticizing oil and a block copolymer or other elastomer that combines with oil in the same manner. One source of elastomeric gels is disclosed in a series of patents to John Chen. These include U.S. Pat. Nos. 4,369,284; 4,618,213; 5,153,254; 5,262,468; 5,334,646; and 5,336,708. These patents describe a variety of gelatinous compositions using an admixture of poly(styrene-ethylene-butylene-styrene) triblock copolymers having styrene end block to ethylene and butylene center blocks with various ratios as disclosed, plus high levels of plasticizing oils ranging from 300 to 1600 parts of oil per 100 parts of copolymer. The products may be generically referred to as SEBS gels. Of course, with a wide range for the oil to polymer ratio, products having many different properties are produced, depending on the specific ratio chosen. For the purposes of this invention, a gel may be produced using the general resilience and hardness of human flesh, particularly in a human orifice that is being duplicated for use herein.

Preferred elastomeric gels are disclosed in a copending patent application filed of even date herewith, entitled GEL COMPOSITION, by Elbert Davis, the disclosure of which is incorporated herein by reference. The Davis gel composition comprises a styrene-ethylene propylene-styrene block copolymer, hereinafter called SEPS, that is highly extended with oil such as mineral oil, such that the ratio of SEBS to oil is carefully controlled to simulate the tactile feel of flesh. Preferred are SEPS polymers having a number average molecular weight of at least 150,000 to 200,000.

The SEPS is highly extended with oil such as mineral oil, so the ratio of SEPS to oil is carefully controlled to simulate the tactile feel of flesh. White mineral oil, naphthenic oils, and synthetic oils such as Shellflex® 371, manufactured by Shell Chemical Co. are preferred. Other oils include petroleum paraffinic oils, petroleum naphthenic oils, synthetic polybutene oils, synthetic polypropene oils, synthetic polyterpene oils and mixtures thereof.

The basic components of the Davis gelatinous composition, namely the oil and the polymer, use a ratio defined as:

$$R = \frac{\text{quantity of oil}}{\text{quantity of } SEPS}$$

The ideal value for R as defined above is 14, while 13 to 15 are quite acceptable and form gels where the composition has the tactile feel of human flesh, depending on the specific part of the body being replicated. It has also been found that in most cases, depending of course on specific molecular weight SEPS polymers and specific oils, a value of R of 10 produces a gelatinous composition that is too hard to simulate the tactile feel of flesh. Also, a value of R of 18 is too soft to accomplish the goal of simulating the tactile feel of flesh. Thus the preferred range for R is between about 12 and 16 or 17, and the most preferred range for R, as defined above, is between about 13 and 15.

The gel that is used for insert 25 may also be coated with various materials to assist in optimizing the surface characteristics, as long as the gel has the resilience and hardness that human flesh has, such as by dusting with fine corn starch powder, amorphous silica powder, sodium aluminosilicate or talc. Another coating composition is described in U.S. Pat. No. 5,164,231 by Elbert Davis, as well as in divisional U.S. Pat. No. 5,254,391 and continuation-in-part U.S. Pat. No. 5,302,440, the disclosures of all three patents being incorporated herein by reference.

Other components may also be added, such as pigments such as titanium dioxide and dyes of various colors such as purple dye to render the appearance most natural in color. Surface tackiness may be reduced by dusting with fine corn starch, or other materials may be added such as a wax or polypropylene homopolymers to reduce surface tack. All that is needed is that the elastomeric gel replicate the feel of human flesh and can be molded into a shape as described herein for use with the outer shell.

The insert is molded using conventional molding techniques. A metal shaft may be used in the center of the insert during molding to provide a central portion 28 to accommodate the user. As noted in FIG. 4, insert 25 has an end 27 that simulates an orifice of a human female. It may, alternatively, simulate another orifice or have no appearance other than the opening that is to be used. Primarily, depending upon the intended end use of the product, the end 27 may replicate a vagina, a rectal orifice or a mouth and lips. The degree of replication of the visual aspects of the orifice is a matter of choice, depending in part on the intended use. For medical purposes, a simple rounded end with a central passage may be specific. Other users may require or prefer more accurate renditions of that part of the anatomy.

Figure 5:
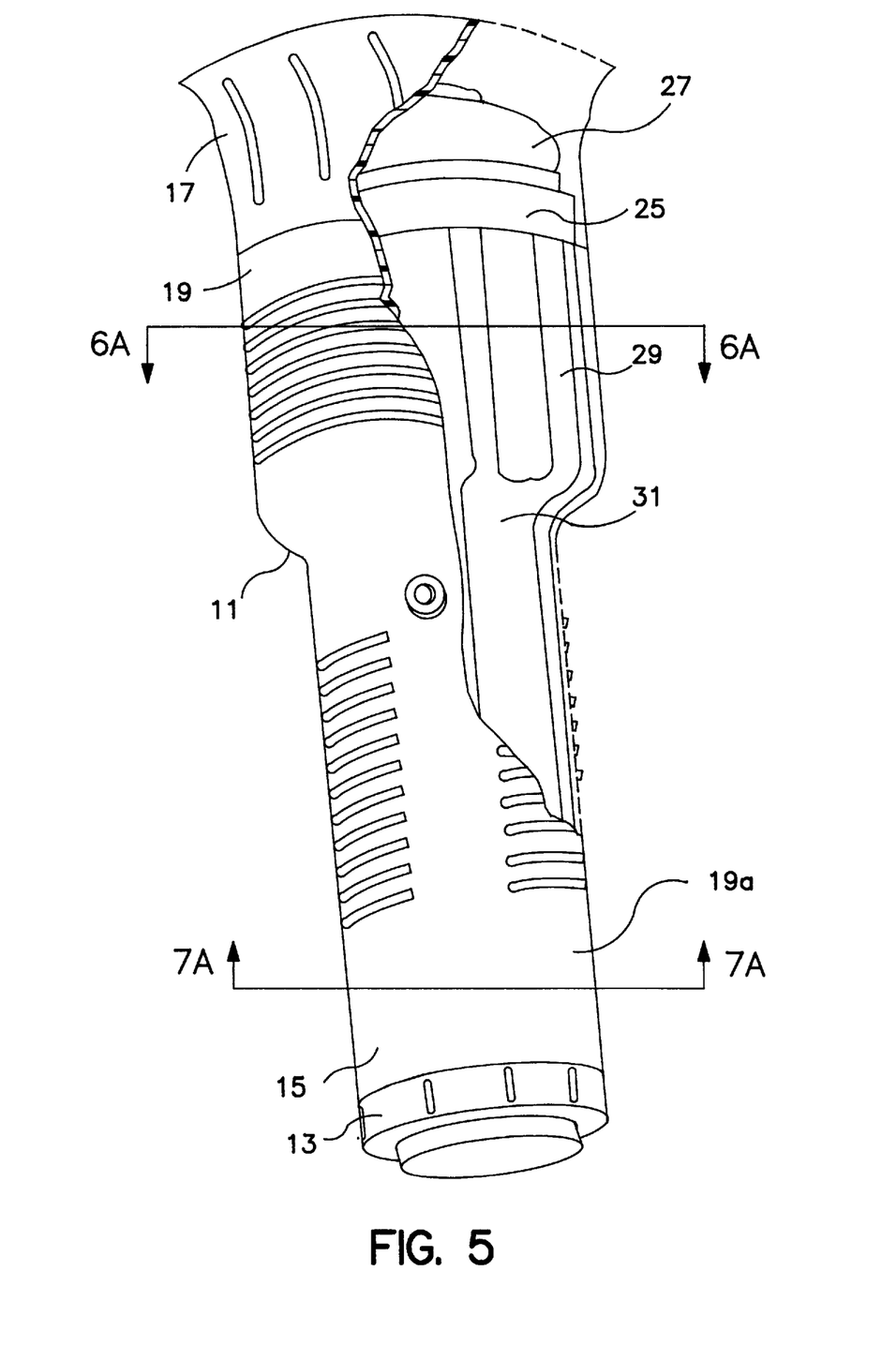
FIG. 5 is a perspective view, partially cut away, of the preferred insert or interior portion of the device shown in FIG. 1, with the insert of FIG. 4 placed within the device.

FIG. 4 shows that the molded insert 25 includes a plurality of radially extending raised ribs or high points 29. Ribs 29 engage or conform to the shape of the interior of flashlight 11, as seen in FIG. 5. The rest of insert 25 consists of radially extending low spots 31 that do not contact the inside of flashlight 11, also shown in FIGS. 4 and 5. These low spots provide for expansion of the central chamber 28 during use.

The insert 25 is of sufficient size to accommodate penetration by a human male sex organ when aroused. In fact, several sizes can be designed to accommodate a human male sex organ. Size may be varied by having larger or smaller central passages 28. Alternatively, the degree of firmness or compression of the elastomeric gel itself may be altered, perhaps by adjusting the ratio of oil to block copolymer or by selection of different oils or copolymers. Obviously a softer, more compressible material will accommodate a larger object being inserted.

Figure 6A:
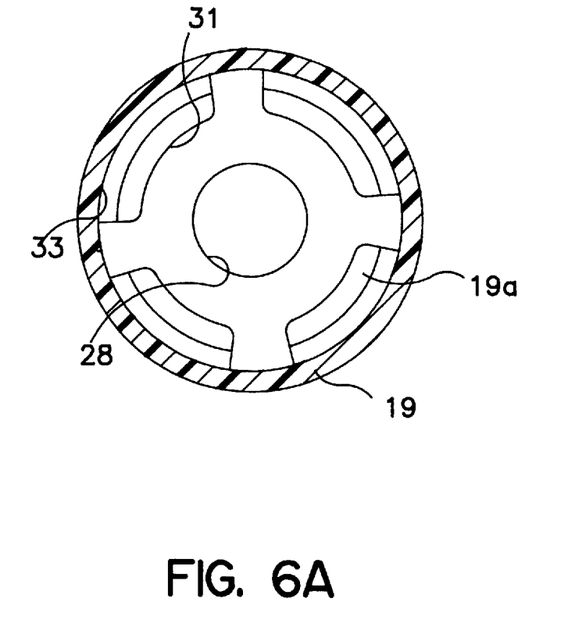
FIGS. 6A and 6B are end, sectioned views taken along the line 6—6 of FIG. 5, showing the end of the device, both with and without the insert of FIG. 4 in the device.
Figure 6B:
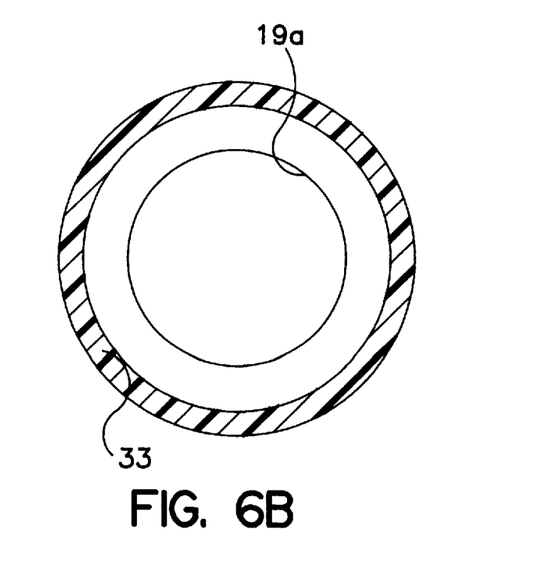

FIGS. 6A and 6B illustrate the small end 15 of flashlight 11. In FIG. 6B, the insert is not present and center passage 33 is empty. In FIG. 6A, insert 25 has been fitted into center passage 33 such that radially extending raised ribs 29 engage the surface of passage 33 to provide a friction tight fit. Radially extending low spots 31 are free to expand and resist the efforts of the user to stimulate the user and duplicate the feel of the orifice it is intended to replicate. When insert 25 is formed, the central passage 28 accommodates a mold or forming agent which is typically cylindrical in shape, such as a metal rod, such that most, say 95–98% of its length is cylindrical, and the last end—about which end 27 is formed—is tapered to flat, to provide a slit shape to end 27. The flat end of the metal rod hooks into the mold face to align the rod in the mold itself. FIG. 6A illustrates this slit 28a, which is the underside of slit 28 in FIG. 7A.

Figure 7A:
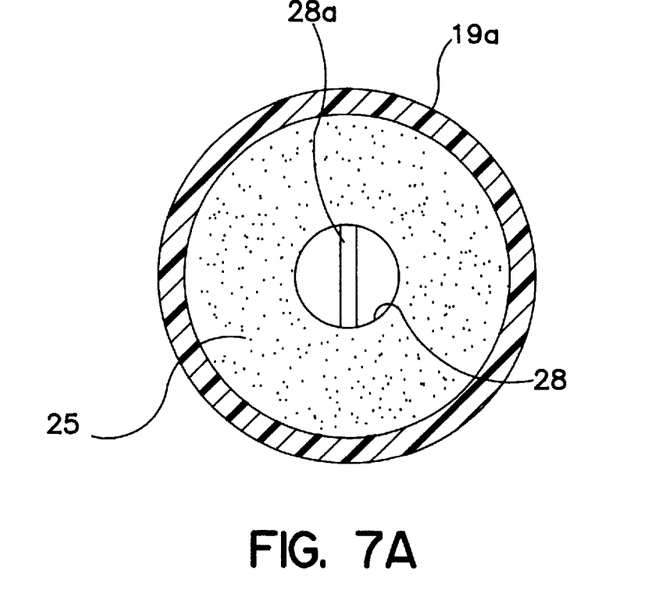
FIGS. 7A and 7B are end, sectioned views taken along the line 7—7 of FIG. 5, showing the end of the device, both with and without the insert of FIG. 4 in the device.
Figure 7B:
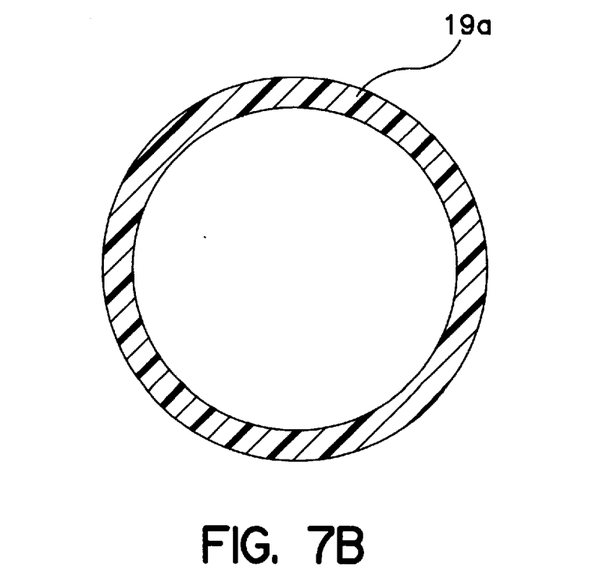

FIGS. 7A and 7B illustrate the larger end 19 of flashlight 11, showing in FIG. 7B that central passage 33 extends along the entire axis of flashlight 11. FIG. 7A shows the location of insert 25, with radially extending raised ribs 29 in contact with central passage surface 33 and radially extending low points 31 free for expansion or compression to accommodate the user. Central passage 28 extends substantially the entire length of insert 25, so as to provide adequate space for use by a variety of male organ sizes.

Prior to use, the device has been stored in a suitably private location, but due to its ordinary appearance, is not likely to incite the curiosity of children or others in the household or medical facility. Use of the device is simple. A male wishing for discreet and camouflaged collection of his sperm using a device having an outward appearance that is innocuous and portable merely takes the device to the place of intended use, such as a private office at a medical facility, or wherever the user is assured the necessary privacy. The large lens cap end 27 is removed, exposing end 17 of the insert 25. Once the male has used the device, insert 25 may be removed from central passage 33 of flashlight 11 for further collection of semen. It is also ready to be cleaned.

While particular embodiments of the present invention have been illustrated and described, it is not intended to limit the invention, except as defined by the following claims.

I claim:

1. A device useful for discreet and camouflaged collection of sperm from human males, comprising:
   an outer shell having an inside chamber and an exterior with the appearance of a first device having, said shell having openings to provide access to said inside chamber;
   at least one removable cap on said shell for enclosing at least one end of said inside chamber, said cap having an exterior appearance compatible with said device;
   vent means for providing for release of air in said device;
   an insert formed from an elastomeric gel having simulating human flesh of the type forming sexually receptive orifices and removeably mountable into said inside chamber upon removal of said cap, said insert having a first end for insertion into said inside chamber and having a second end having an opening providing an orifice, said second end being positioned to be exposed upon removal of said cap.

2. The device of claim 1, wherein said elastomeric gel is formed from a mixture of plasticizing oil and a block copolymer selected from styrene ethylene butylene styrene block copolymers and styrene ethylene propylene styrene block copolymers.

3. The device of claim 2, wherein said elastomeric gel is formed from a mixture of 5–9% by weight of said block copolymer and 90–94% by weight of said plasticizing oil, and trace amounts of pigments and fillers.

4. The device of claim 1, wherein said device has the appearance of a flashlight.

5. The device of claim 1, wherein said insert includes a central passage sized to accommodate a human male sex organ, said insert providing at least a cushioning amount of said elastomeric gel.

6. The device of claim 5, wherein said insert includes radially extending high points along its length for engagement with said chamber and radially extending low points for expansion of said central passage during use.

7. The device of claim 1, wherein said vent means comprises a second cap removable mounted on the other end of said device.

8. A device useful for discreet and camouflaged collection of sperm from human males, comprising:

an outer shell having an inside chamber and an exterior with the appearance of a first device having, said shell having openings to provide access to said inside chamber;

at least one removable cap on said shell for enclosing at least one end of said inside chamber, said cap having an exterior appearance compatible with said device;

vent means for providing for release of air in said device;

an insert formed from an elastomeric gel having simulating human flesh of the type forming sexually receptive orifices and removeably mountable into said tubular inside chamber upon removal of said cap, said insert having a first end for insertion into said inside chamber and having a second end having an opening providing an orifice, said insert including a central passage sized to accommodate a human male sex organ, said insert providing at least a cushioning amount of said elastomeric gel and having radially extending high points along its length for engagement with said chamber and radially extending low points for expansion of said central passage during use, said second end being positioned to be exposed upon removal of said cap.

9. The device of claim 8, wherein said elastomeric gel is formed from a mixture of plasticizing oil and a block copolymer selected from styrene ethylene butylene styrene block copolymers and styrene ethylene propylene styrene block copolymers.

10. The device of claim 9, wherein said elastomeric gel is formed from a mixture of 5–9% by weight of said block copolymer and 90–94% by weight of said plasticizing oil, and trace amounts of pigments and fillers.

11. The device of claim 8, wherein said device has the appearance of a flashlight.

12. The device of claim 8, wherein said vent means comprises a second cap.

* * * * *